(12) United States Patent
Reeker et al.

(10) Patent No.: US 10,000,440 B2
(45) Date of Patent: Jun. 19, 2018

(54) INFLUENCING THE VISCOSITY OF N-BUTENE-BASED ESTER MIXTURES BY CONTROLLED USE OF ETHENE IN THE PREPARATION OF THE ESTER PRECURSORS

(71) Applicant: Evonik Degussa GmbH, Essen (DE)

(72) Inventors: Helene Reeker, Dortmund (DE); Guido Stochniol, Haltern am See (DE); Dietrich Maschmeyer, Recklinghausen (DE); Horst-Werner Zanthoff, Mülheim a.d. Ruhr (DE); Jörg Schallenberg, Dorsten (DE); Frank Geilen, Haltern am See (DE); Katrin Marie Dyballa, Recklinghausen (DE); Dirk Fridag, Haltern am See (DE); Stephan Peitz, Oer-Erkenschwick (DE); Lena Altmann, Recklinghausen (DE); Robert Franke, Marl (DE)

(73) Assignee: Evonik Degussa GmbH, Essen (DE)

(*) Notice: Subject to any disclaimer, the term of this patent is extended or adjusted under 35 U.S.C. 154(b) by 0 days. days.

(21) Appl. No.: 15/356,507

(22) Filed: Nov. 18, 2016

(65) Prior Publication Data

US 2017/0144959 A1    May 25, 2017

(30) Foreign Application Priority Data

Nov. 19, 2015  (EP) .................................... 15195302

(51) Int. Cl.
| | | |
|---|---|---|
| C07C 67/08 | (2006.01) | |
| C07C 2/24 | (2006.01) | |
| C07C 29/141 | (2006.01) | |
| C07C 45/50 | (2006.01) | |

(52) U.S. Cl.
CPC .............. C07C 67/08 (2013.01); C07C 2/24 (2013.01); C07C 29/141 (2013.01); C07C 45/50 (2013.01); C07C 45/505 (2013.01); C07C 2521/12 (2013.01); C07C 2523/755 (2013.01); Y02P 20/52 (2015.11)

(58) Field of Classification Search
CPC ......... C07C 67/08; C07C 2/24; C07C 29/141; C07C 45/505; C07C 2521/12; C07C 2523/755; C07C 45/50; C07C 11/02; C07C 31/125; C07C 47/02; C07C 69/80
See application file for complete search history.

(56) References Cited

U.S. PATENT DOCUMENTS

| | | | |
|---|---|---|---|
| 2,581,228 A | 1/1952 | Bailey et al. | |
| 5,438,027 A * | 8/1995 | Reagen ..................... | C07C 2/30 502/117 |
| 6,433,242 B1 | 8/2002 | Wiese | |
| 7,361,714 B2 | 4/2008 | Grass et al. | |
| 7,524,997 B2 | 4/2009 | Kaizik et al. | |
| 7,632,961 B2 | 12/2009 | Bueschken et al. | |
| 7,683,204 B2 | 3/2010 | Büschken et al. | |
| 8,044,229 B2 | 10/2011 | Maschmeyer et al. | |
| 9,206,105 B2 | 12/2015 | Christiansen et al. | |
| 9,272,973 B2 | 3/2016 | Fridag et al. | |
| 9,409,844 B2 | 8/2016 | Christiansen et al. | |
| 9,428,433 B2 | 8/2016 | Fridag et al. | |
| 9,556,096 B2 | 1/2017 | Christiansen et al. | |
| 2004/0238787 A1* | 12/2004 | Wiese ..................... | C07C 69/80 252/182.28 |
| 2006/0041167 A1 | 2/2006 | Grass et al. | |
| 2010/0137486 A1 | 6/2010 | Bueschken et al. | |

(Continued)

FOREIGN PATENT DOCUMENTS

| | | |
|---|---|---|
| CN | 101774912 | 1/2013 |
| DE | 102008007081 A1 | 8/2009 |
| EP | 1029839 A1 | 8/2000 |
| EP | 1219584 B1 | 10/2003 |
| EP | 1186593 B1 | 11/2005 |
| EP | 1300388 B1 | 12/2005 |
| EP | 2947064 A1 | 11/2015 |
| WO | WO1995014649 * | 6/1995 |
| WO | 2003029180 A1 | 4/2003 |
| WO | 2013168106 | 11/2013 |
| WO | 2014131623 | 9/2014 |
| WO | 2014207034 A1 | 12/2014 |

OTHER PUBLICATIONS

Geilen, et al.; Ullmann's Encyclopedia of Industrial Chemistry. Published Online: Jan. 31, 2014 DOI: 10.1002/14356007.a04_483.pub3.

Friedlander, et al.; Make plasticizer olefins via n-butene dimerization. Hydrocarbon Processing, Feb. 1986, pp. 31 to 33.

Franke, et al.; "Applied Hydroformylation", Chem. Rev., 2012 (112), p. 5675-5732, DOI:10.1021/cr3001803.

Falbe, et al.; Alcohols Aliphatic in Ullmann's Encyclopedia of Industrial Chemistry, 2013.

Sanfilippo, et al.; Hydrogenation and Dehydrogenation in Ullmann's Encyclopedia of Industrial Chemistry, 2009.

*Primary Examiner* — Yevgeny Valenrod
*Assistant Examiner* — Blaine G Doletski
(74) *Attorney, Agent, or Firm* — Michael Best Friedrich LLP (57) ABSTRACT

The invention relates to a process for preparing an ester mixture, in which an n-butene-containing feed mixture having a composition which changes over time is first oligomerized and then converted by hydroformylation, hydrogenation and esterification to an ester mixture. In this process, an approximation of the actual viscosity of the ester mixture is determined. The problem that it addresses is that of specifying a comparatively simple process which enables conversion of an n-butene with a variable composition over time to an ester mixture having a viscosity which can be kept very substantially constant over a long period even when an inconstant $C_4$ source which delivers fluctuating qualities over this period is utilized. This is achieved through controlled use of a second raw material, namely ethene. It has been found that the viscosity of n-butene-based ester mixtures can be influenced by controlled use of ethene in the preparation of the ester precursors. Specifically, the invention proposes two measures by which the ethene can be used: either directly as $C_2$ olefin or as $C_8$ olefin after prior separate oligomerization.

11 Claims, 8 Drawing Sheets

(56) References Cited

U.S. PATENT DOCUMENTS

| | | |
|---|---|---|
| 2013/0158321 A1* | 6/2013 | Olivier-Bourbigou ... C07C 2/24 585/329 |
| 2015/0336093 A1 | 11/2015 | Dyballa et al. |
| 2015/0336861 A1 | 11/2015 | Geilen et al. |
| 2016/0002136 A1 | 1/2016 | Lueken et al. |
| 2016/0207848 A1 | 7/2016 | Stochniol et al. |
| 2016/0207849 A1 | 7/2016 | Stochniol et al. |
| 2016/0257630 A1 | 9/2016 | Stochniol et al. |

\* cited by examiner

INFLUENCING THE VISCOSITY OF N-BUTENE-BASED ESTER MIXTURES BY CONTROLLED USE OF ETHENE IN THE PREPARATION OF THE ESTER PRECURSORS

The invention relates to a process for preparing an ester mixture in which an n-butene-containing feed mixture having a composition which varies over time is subjected to a first oligomerization to obtain an oligomerizate and at least some of the butene oligomers present in the oligomerizate are hydroformylated to aldehydes, of which at least some are hydrogenated by subsequent hydrogenation to an alcohol mixture which is then converted to an ester mixture, and in which an approximation of the actual viscosity of the ester mixture is determined.

The ester mixtures being discussed here serve as plasticizers for polyvinyl chloride (PVC). Examples of such ester mixtures which are produced on a large industrial scale are diisononyl phthalate (DINP), isononyl benzoate (INB) and diisononyl cyclohexane-1,2-dicarboxylate (DINCH).

Figure 1A:
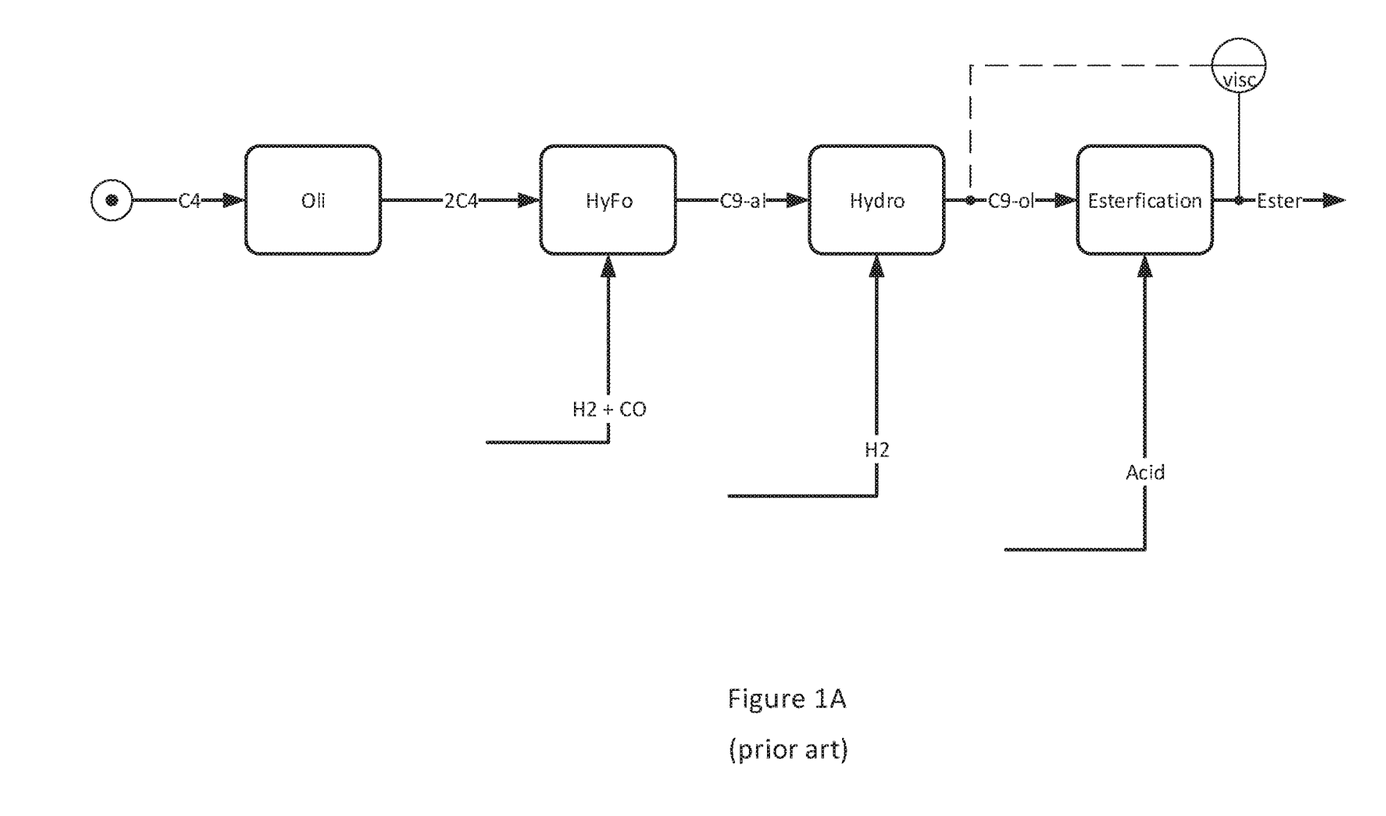
FIG. 1A: Industrial production of the DINP ester mixture from C4 raw materials according to the prior art.

The industrial production of DINP is shown in simplified form in FIG. 1A.

FIG. 1A: Industrial production of the DINP ester mixture from $C_4$ raw materials according to the prior art The raw material source used is butenes, more specifically n-butene. The butenes are alkenes (synonym: olefins) having four carbon atoms, which are consequently also referred to in the art as $C_4$ olefins. In the figures, the abbreviation C4 is used for these. There exist the four structurally isomeric $C_4$ olefins isobutene, 1-butene, cis-2-butene and trans-2-butene. Isobutene is a branched olefin; the three linear $C_4$ olefins 1-butene, cis-2-butene and trans-2-butene are often referred to collectively as n-butene. n-Butene should thus be understood to mean a mixture of linear butenes and contains at least one of the three substances 1-butene, cis-2-butene and trans-2-butene, but not necessarily all three of these substances. For example, a mixture of the two 2-butenes which is free of 1-butene can also be regarded as n-butene.

$C_4$ olefins are obtained, inter alia, in the steamcracking of naphtha (called crack-C4). Because of changes in the raw material basis, the availability of crack-C4 has declined in recent years, and so other $C_4$ sources are increasingly being developed, for instance from fluid-catalytic naphtha cracking (FCC-C4) or from the dehydrogenation of butane.

The exact composition of the n-butene which is used as starting material for the preparation of the ester mixture depends significantly on the raw material source available. Moreover, the upstream workup of the $C_4$ raw material in which other materials of value such as 1,3-butadiene, isobutene and 1-butene are exhausted and disruptive substances are removed affects the composition of the n-butene.

An introduction into the chemistry of the $C_4$ olefins and the industrial utilization thereof can be found in:
Geilen, F. M., Stochniol, G., Peitz, S. and Schulte-Koerne, E.: Butenes. Ullmann's Encyclopedia of Industrial Chemistry. Published Online: 31 Jan. 2014 DOI: 10.1002/14356007.a04_483. pub3

In the preparation of DINP, in a first reaction step, the linear butenes are subjected to an oligomerization (Oli).

Oligomerization is understood to mean the reaction of hydrocarbons with themselves, forming correspondingly longer-chain hydrocarbons. For example, the oligomerization of two olefins having three carbon atoms (dimerization) can form an olefin having six carbon atoms. If, in contrast, three olefins having three carbon atoms are joined to one another (trimerization), the result is an olefin having nine carbon atoms.

If butenes are subjected to an oligomerization, the result is essentially olefins having eight carbon atoms ($C_8$ olefins, often called "dibutenes"), olefins having twelve carbon atoms ($C_{12}$ olefins, "tributenes") and, to a smaller extent, olefins having more than twelve carbon atoms ($C_{12+}$ olefins).

The product of the oligomerization, called the oligomerizate, thus contains different butene oligomers, namely dibutenes, tributenes, higher oligomers and unconverted butenes. For the production process being outlined here, only the dibutenes (2C4) are of interest. They are separated by distillation from the oligomerizate. For the sake of simplicity, however, this is not shown in the figures.

Details of the industrially practised oligomerization of $C_4$ olefins can be found in the non-patent literature, for example in:
R. H. Friedlander, D. J. Ward, F. Obenaus, F. Nierlich, J. Neumeister: Make plasticizer olefins via n-butene dimerization. Hydrocarbon Processing, February 1986, pages 31 to 33.

Within the patent literature, for example, DE102008007081A1 describes an oligomerization of butenes. EP1029839A1 is concerned with the fractionation of the oligomerizate into the individual butene oligomers.

The oligomerization is followed by, as the second reaction step, a hydroformylation (HyFo). This involves reacting the dibutenes (2C4) with synthesis gas ($H_2$+CO)—which is a mixture of hydrogen ($H_2$) and carbon monoxide (CO)—to give a mixture of aldehydes having nine carbon atoms (C9-al).

A good overview of the general state of hydroformylation of olefins can be found in
R. Franke, D. Selent, A. Börner, "Applied Hydroformylation", Chem. Rev., 2012 (112), p. 5675-5732, DOI: 10.1021/cr3001803.

The hydroformylation gives rise not only to the desired aldehydes (C9-al) but also to unwanted by-products which have to be separated from the hydroformylation reaction mixture. The workup of hydroformylation mixtures is not trivial; cf. WO2014131623. Since it does not matter here how the aldehydes are obtained from the hydroformylation reaction mixture, this is not shown in the figures.

The $C_9$-aldehydes are then hydrogenated in a third reaction step to give alcohols having nine carbon atoms (C9-ol). In the hydrogenation (Hydro), hydrogen ($H_2$) is added onto the aldehyde, so as to form an alcohol. Since a mixture of different aldehydes having nine carbon atoms (C9-al) is being hydrogenated here, the hydrogenation affords a mixture of various alcohols having nine carbon atoms (C9-ol) which is called isononanol, INA for short. Isononanol is a mixture of isomeric nonyl alcohols, for example n-nonanol, and singly and/or multiply branched nonanols, such as methyloctanol in particular. A more detailed description of the hydrogenation of aldehydes prepared by hydroformylation can be found in EP1219584B1.

In the last production step, the esterification, the alcohol mixture (C9-ol) is converted to an ester mixture (Ester). Esters are generally formed by addition of acid to alcohols or by transesterification of an existing ester in the presence of an alcohol.

In the industrial version, the nonanol mixture is esterified with phthalic acid or phthalic anhydride (Acid). The ester mixture used as plasticizer is then the diisononyl phthalate (DINP). This can in principle also be prepared by transesterification of a dialkyl phthalate with isononyl alcohol; in this context, dimethyl phthalate in particular is used.

Details of such esterification processes can be found in EP1186593B1 and EP1300388B1.

The viscosity of the ester mixture is crucial to the product quality of the plasticizer produced. Depending on the end use of the plasticized PVC, either a high viscosity or a low viscosity is required. In both cases, what the processors of plasticizers want is a very substantially constant viscosity of the ester mixtures used over long production periods, since it is undesirable to have to adapt formulations, once they are fixed, to varying product qualities. The manufacturers of plasticizers are consequently expected to supply their ester mixtures with constant viscosity over long periods of time.

For the purpose of quality assurance, the viscosity of the ester mixture produced (Ester) is measured with an instrument (vise), such that an approximation of the actual viscosity of the ester mixture is obtained, taking account of the measurement errors.

The viscosity of the ester mixtures is determined to a crucial degree by the isomer distribution of the alcohol mixture to be esterified. This relationship is illustrated in EP1430014B1, and a formula is actually specified by which the viscosity of the later ester mixture can be calculated from the analysis of the esterified alcohol mixture. In FIG. 1A, the dotted line between the output of the hydrogenation (C9-ol) and the instrument (vise) indicates such a mathematical determination of the approximation of the actual viscosity of the ester mixture on the basis of the composition of the alcohols.

The composition of the alcohol mixture depends in turn on the isomer distribution of the hydroformylated butene oligomers. A measure of the isomer distribution of butene oligomers is the degree of branching, measured as the iso index; cf. U.S. Pat. No. 6,433,242B1.

The degree of branching of the butene oligomers in turn arises from the composition of the oligomerization feedstocks: thus, a $C_4$ olefin mixture particularly rich in 1-butene leads to butene oligomers with a low branching level, whereas those $C_4$ feedstocks that consist predominantly of cis-2-butene and trans-2-butene lead to high iso indices without further measures; cf. WO2014/207034A1.

Ultimately, in the production sequence shown in FIG. 1A, the composition of the $C_4$ olefins used is thus responsible for the viscosity of the ester mixture prepared.

Provided that the source of the $C_4$ olefins affords a reliable quality—i.e. a $C_4$ mixture with a constant composition over time—and the processing operations are under control, it is possible to prepare ester mixtures with constant viscosity.

If, however, the inconstant source which affords $C_4$ mixtures constantly having varying composition is to be utilized, it is barely possible still to achieve a constant plasticizer quality with a conventional process regime.

Since reliable and high-grade $C_4$ sources such as naphtha steamcrackers are becoming ever rarer, the manufacturers of $C_4$-based products are increasingly moving to alternative raw material sources having a low-grade composition compared to crack-C4.

For instance, WO2014/207034A1 describes how a low-grade $C_4$ mixture containing barely any 1-butene can still be used to make oligomers suitable for plasticizer production.

A further disadvantage of alternative $C_4$ sources is that the composition of the raw material streams supplied is subjected to significant changes over time. Especially when the 1-butene content which has a significant effect on the viscosity is changing constantly, it is difficult to assure homogeneous plasticizer quality.

The application EP 15168100.4 or U.S. Ser. No. 14/717,183, which was yet to be published at the filing date, describes technical measures which make it possible to utilize a $C_4$ source which is variable over time for the preparation of plasticizer esters. All these measures are aimed at the process regime and are technically very complex.

In view of all the above, the problem addressed by the invention is that of specifying a comparatively simple process which enables conversion of an n-butene with a variable composition over time to an ester mixture having a viscosity which can be kept very substantially constant over a long period even when an inconstant $C_4$ source which delivers fluctuating qualities over this period is utilized.

This is surprisingly achieved through controlled use of a second raw material, namely ethene. It has been found that the viscosity of n-butene-based ester mixtures can be influenced by controlled use of ethene in the preparation of the ester precursors.

The invention therefore provides for the influencing of the viscosity of n-butene-based ester mixtures by controlled use of ethene in the preparation of the ester precursors.

Specifically, the invention proposes two measures by which the ethene can be used: either directly as $C_2$ olefin or as $C_8$ olefin after prior separate oligomerization.

In a first embodiment of the invention, as a function of the approximation of the actual viscosity of the ester mixture determined, ethene oligomers which are obtained by subjecting an n-butene-free, ethene-containing feed mixture to a second oligomerization conducted separately from the first oligomerization are added in a controlled manner to the butene oligomers to be hydroformylated. One process that proceeds in the second oligomerization is tetramerization of ethene, and so $C_8$ olefins that form through joining of four $C_2$ olefins are obtained. In the oligomerization of ethene, as well as the $C_8$ olefins, $C_4$, $C_6$ and higher olefins are also obtained, but these need not all be mixed with the oligomerizate of the butene oligomerization. If the aim of the hydroformylation is the preparation of $C_m$ aldehydes, the $C_{m-1}$ olefins are separated from the oligomerizate of the ethene oligomerization and mixed with the oligomerizate from the butene oligomerization. If the aim is thus to prepare $C_9$ aldehydes in the hydroformylation, the tetramers from the $C_2$ oligomerization are mixed with the $C_8$ olefins from the $C_4$ oligomerization (dibutene). The mixture thus obtained thus contains two kinds of $C_8$ olefins, namely firstly butene dimers and secondly ethene tetramers. This mixture of $C_8$ olefins of different genesis is then subjected to the hydroformylation.

The effect of the addition of the $C_2$-based oligomerizate is that the tetramers of ethene have a lower degree of branching than the dimers of butene, and that the mixing of the minimally branched $C_2$ oligomers and the more highly branched $C_4$ oligomers gives rise overall to a $C_8$ oligomer mixture having lower branching. This leads in turn to a lower viscosity of the ester mixture prepared therefrom.

In order to lower the viscosity of the later ester mixture, the proportion of ethene oligomers in the $C_8$ mixture should accordingly be increased relative to the butene oligomers. If, conversely, the viscosity should be increased, the addition of ethene tetramers to the substrate to be hydroformylated is reduced.

In a second embodiment of the invention, as a function of the approximation of the actual viscosity of the ester mixture determined, ethene is added in a controlled manner to the n-butene-containing feed mixture, such that the first oligomerization is a co-oligomerization of ethene and n-butene. Co-oligomerization in this context means that the ethene and the butene are oligomerized simultaneously in the same reaction vessel over the same catalyst. The ethene oligomers and the butene oligomers are then mixed in situ in the reactor and not at a later stage by blending of the oligomers obtained separately. At the same time, oligomerizates containing both butene and ethene are also formed in the reactor. Thus, C8 olefins can be formed from two butene molecules, or from four ethene molecules, or else from two ethene molecules and one butene molecule.

The effect on the viscosity is the same: the higher the proportion of ethene in the co-oligomerization, the lower the viscosity of the later esters. Control is then accordingly effected via the degree of mixing of ethene into the butene-containing feed stream.

The basic idea of the invention that connects the two embodiments is thus to upgrade the varying $C_4$ feed mixture or the butene oligomers derived therefrom in a controlled manner by adding ethene or ethene oligomers, since it is possible in this way to influence the resulting viscosity of the ester mixture.

The particular advantage of this process is considered to be that there is barely any change in the actual production processes, with influence instead on the processed substances. In this respect, the invention differs from the measures described in EP 15168100.4 or U.S. Ser. No. 14/717, 183, which do not influence the streams of matter but alter plant parameters in a complex manner.

One disadvantage of this process in principle is admittedly that there is reliance on a second raw material source which provides the $C_2$ olefin ethene, and does so in a very substantially uniform quality.

However, ethene is a readily available petrochemical since it is required in large volumes for the preparation of polyethylene. Moreover, ethene can be obtained from unconventional natural gas deposits. There are therefore various ways of arriving at the ethene required for the performance of the process. The extra costs associated with the $C_2$ source are compensated for in that the process is able to utilize a low-grade $C_4$ source which is much less expensive than the high-grade and hence costly $C_4$ sources that have been utilized to date.

In a first development of the variant of the invention in which ethene oligomers are added to the oligomerizate of the n-butene-containing feed mixture, the ethene oligomers are obtained by subjecting an n-butene-free, ethene- and hexene-containing feed mixture to the second oligomerization conducted separately from the first oligomerization, such that the second oligomerization is a co-oligomerization of ethene and hexene. Hexene in this context is understood to mean a collective term for one or more olefins having six carbon atoms, such as 1-hexene or n-hexene. The co-oligomerization of ethene and the $C_6$ olefin has the effect that the hexene functions as solvent for the ethene, as a result of which it is possible to better control the reaction conditions. This effect is described in European patent application 15151621.8, which was yet to be published at the filing date of the application.

It is advisable to separate the hexene solvent from the desired ethene-based $C_8$ oligomers before they are mixed with the dibutene. Otherwise, ballast would be carried along, which leads to side reactions in the later stages and can lower the quality of the ester.

An important technological advantage of the co-oligomerization of ethene with hexene is that it can be effected in the liquid phase. This is because the oligomerization is highly exothermic and, by using hexene as liquid solvent, it is easily possible to remove the heat of reaction. The butene oligomerization also takes place in the liquid phase. A further advantage of liquid ethene oligomerization is that it is possible to use the same reactors and plant components therefor as in the butene oligomerization, such that the complexity of the plant can be kept low.

Hexene is barely obtainable as an isolated raw material. However, it can be obtained from the standard $C_2$ and $C_3$ sources by oligomerization. Therefore, the hexene is sourced from a third oligomerization which is conducted separately from the first and second oligomerizations, in which ethene is trimerized or in which propene is dimerized.

Rather than preparing the hexene separately, it can also be sourced from the ethene oligomerization which is present in any case: the second oligomerization, which always contains ethene, always gives rise to hexene as well, irrespective of whether any other olefin or any solvent is also present. Therefore, hexene is obtained in the first embodiment as a by-product in the ethene trimerization, and in the second embodiment as a by-product of the co-oligomerization of n-butene with ethene. In one variant of the process, therefore, the hexene is sourced from the second oligomerization.

The advantage of the co-oligomerization of ethene and hexene is that the trimers of ethene that are obtained as a by-product in any case can be used as a solvent in a useful manner. In addition, the hexene as solvent, in contrast to other conceivable solvents, for example isobutane, enables more favourable conditions with regard to the distillative removal, since it is not necessary to remove such great amounts of solvent overhead at elevated pressures. This lowers the costs for installation and operation of the solvent removal.

In a preferred development of the embodiment of the invention in which ethene and butene are oligomerized separately, the ethene oligomerization is conducted in the presence of an inert liquid solvent. The ethene is then at least partly dissolved in the liquid solvent. The ethene oligomers are then also present dissolved in the solvent and should be removed prior to mixing with the butene oligomers. The solvent can then be recycled and mixed with fresh ethene. The advantage of oligomerization in the presence of the inert solvent is that the reaction conditions can be better controlled. Moreover, it is simpler in this way to oligomerize the volatile ethene in the liquid phase over a solid heterogeneous catalyst and hence to achieve high process intensity. Useful inert solvents are those that are sufficiently unreactive that they do not take part in the oligomerization. Specifically, these may be propane, isobutane, pentane, hexane or heptane or mixtures of these alkanes. However, only those alkanes that have either a higher or lower boiling point than the ethene oligomers should be mixed, such that the separation of the ethene oligomers from the solvent does not become too complicated.

Incidentally, it may also be advantageous to use an inert solvent in the $C_2$ oligomerization when it is effected in the presence of reactive hexene.

In a further development of the embodiment in which ethene and butene are oligomerized separately, the controlled addition of the ethene oligomers to the butene oligomers is effected in such a way that a target viscosity of the ester mixture is first fixed, the approximation of the actual viscosity of the ester mixture determined is compared with the target viscosity of the ester mixture, and the amount of the ethene oligomers added to the butene oligomers to be hydroformylated is increased if the approximation of the actual viscosity is greater than the target viscosity, or the amount of the ethene oligomers added to the butene oligomers to be hydroformylated is reduced if the approximation of the actual viscosity is less than the target viscosity.

Accordingly, in the embodiment in which ethene and butene are co-oligomerized, the controlled addition of the ethene to the feed mixture is effected in such a way that a target viscosity of the ester mixture is first fixed, the approximation of the actual viscosity of the ester mixture determined is compared with the target viscosity of the ester mixture, and the amount of the ethene added to the feed mixture is increased if the approximation of the actual viscosity is greater than the target viscosity, or the amount of ethene added to the feed mixture is reduced if the approximation of the actual viscosity is less than the target viscosity. This control approach is based on the finding that viscosity falls with rising ethene content, and vice versa.

The approximation of the actual viscosity of the ester mixture is required in order to be able to assess whether the ethene or ethene oligomer content has to be lowered or increased in order ultimately to make the viscosity of the ester mixture constant. In the simplest case, the determination of the approximation of the actual viscosity of the ester mixture is effected by measurement.

Which actual viscosity is determined by which test method under which conditions to make the approximation is unimportant for the implementation of the invention. The target viscosity is ultimately determined both in terms of its parameter and in terms of its test method by the customers that use the ester mixture. The approximation of the actual viscosity is therefore determined by the method defined for the target viscosity.

For example, it is possible to determine the approximation of the actual viscosity in accordance with ASTM D7042. Within the scope of measurement accuracy, the approximation of the actual viscosity then corresponds to the true actual viscosity.

The measurement of the actual viscosity of the ester mixture requires that the last process step (the esterification) is already complete. In industrial practice, however, the esterification is effected in batchwise mode, while the other preceding reaction steps are conducted continuously. This means that some time passes before the esterification is complete and the viscosity achieved can be measured. In the meantime, however, oligomerization, hydroformylation and hydrogenation continue to run continuously and it is no longer possible to influence the isomer distribution of the alcohol mixture produced in the meantime if the measurement should show an unacceptable deviation from the target viscosity: the batchwise esterification causes a dead time which distinctly reduces the quality of closed-loop control.

In order to avoid this problem, the invention instead proposes determining the approximation of the actual viscosity by calculation, the calculation being based on an analysis of the alcohols. A suitable calculation method by which the composition of the alcohols can be used to determine the viscosity of the later ester mixture is disclosed in EP1430014B1.

A particular advantage of the mathematical determination of the approximation of the actual viscosity via the above formula is that the analysis of the alcohols can be effected in an automated and continuous manner; namely by gas chromatography. Therefore, the viscosity can likewise be determined continuously and virtually without dead time. In this way, it is possible to react at an early stage to variations in the composition of the butenes by adding ethene or ethene oligomer. The quality of closed-loop control is considerably improved.

Alternatively, the approximation of the actual viscosity of the ester mixture can be determined by calculation, the calculation being based on an analysis of the aldehyde mixture. The calculation is effected analogously to the method described in EP1430014B1.

Likewise alternatively, the approximation of the actual viscosity of the ester mixture can be effected by calculation based on an analysis of the oligomers to be hydroformylated. In the determination of the approximation of the actual viscosity, all $C_8$ oligomers have to be taken into account, including those that originate from ethene or have formed through joining of $C_2$ with $C_2$ with $C_4$ or from joining $C_2$ with $C_6$. The calculation is effected analogously to the method described in EP1430014B1.

The present process is intended for utilization of $C_4$ sources which continuously deliver a raw material stream which is subject to variations in time in terms of its composition. Such an inconstant $C_4$ source typically affords an n-butene-containing feed mixture which is composed of a combination of the following substance mass flow rates which vary within the specified substance mass flow rate ranges with a respective rate of variation within the specified range of rates of variation:

| Substance | Substance mass flow rate | Rate of variation |
|---|---|---|
| Isobutene: | 0 kg/s to 1 kg/s | $-0.05$ $g/s^2$ to $0.05$ $g/s^2$ |
| 1-Butene: | 0 kg/s to 6 kg/s | $-0.30$ $g/s^2$ to $0.30$ $g/s^2$ |
| 2-Butene (cis + trans): | 1 kg/s to 13 kg/s | $-0.30$ $g/s^2$ to $0.30$ $g/s^2$ |
| Isobutane: | 0 kg/s to 3 kg/s | $-0.15$ $g/s^2$ to $0.15$ $g/s^2$ |
| n-Butane: | 1 kg/s to 7 kg/s | $-0.30$ $g/s^2$ to $0.30$ $g/s^2$ |
| Other materials: | 0 kg/s to 1 kg/s | $-0.05$ $g/s^2$ to $0.05$ $g/s^2$ |

The rate of variation is understood in mathematical terms to be the differential of the substance mass flow rate with respect to time.

Thus, a stream of the feed mixture according to the specification could deliver 1 kg of 1-butene per second, and this value could vary at a rate of 0.25 $g/s^2$. This means that, within 100 000 seconds (=28 hours), the component mass flow rate of 1-butene content rises up to 3.5 kg/s. Conversely, a decrease in the 1-butene content with a rate of variation of $-0.1$ $g/s^2$ is also in accordance with the specification, and so a 1 kg/s 1-butene stream dries up completely within less than 3 hours (namely within 10 000 seconds), and so the $C_4$ stream is suddenly free of 1-butene. Since all the components are subject to variations with time, there may also be variations in the total mass flow rate. These variations are limited by the limits of the operating range of the particular plant.

In order to compensate for these variations, ethene is used according to the invention in the preparation of the ester precursors. However, this ethene then has to be provided continuously and with low variation, such that the variations of the ethene-containing feed mixture are not superimposed on the variations in the n-butene-containing feed mixture. In principle, the composition of $C_2$ streams does not vary as significantly as that of $C_4$ streams, since only one ethene isomer exists, whereas n-butene is present in three isomeric structures.

Preferably, the ethene used in a controlled manner is sourced from a continuous ethene source which delivers a combination of the following substance mass flow rates which vary within the specified substance mass flow rate ranges with a respective rate of variation within the specified range of rates of variation:

| Substance | Substance mass flow rate | Rate of variation |
| --- | --- | --- |
| Ethene: | 0.1 kg/s to 5 kg/s | $-0.01$ g/s$^2$ to 0.01 g/s$^2$ |
| n-Butene: | 0 kg/s to 0.01 kg/s | $-0.01$ g/s$^2$ to 0.01 g/s$^2$ |
| Other materials: | 0 kg/s to 1 kg/s | $-0.05$ g/s$^2$ to 0.05 g/s$^2$ |

Compared to the specification of the $C_4$ stream, the $C_2$ stream is very substantially constant. For the sake of good order, it has been made clear that the $C_2$ stream contains virtually no n-butene.

All the olefin oligomerizations described here are preferably conducted in the liquid phase in the presence of a solid heterogeneous catalyst containing nickel, silicon and aluminium. A suitable catalyst is disclosed in U.S. Pat. No. 2,581,228.

The hydroformylation, by contrast, is effected in the presence of a homogeneous catalyst system comprising either cobalt or rhodium. Rh-based catalyst systems may additionally comprise an organophosphorus compound as ligand. Suitable catalyst systems are discussed by Franke et al. in their paper cited above.

The output from the hydroformylation is subjected to a hydrogenation in order to convert the aldehydes present to alcohols. The catalytic hydrogenation of aldehydes to alcohols has been broadly described in the literature; it may proceed either with heterogeneous catalysis or with homogeneous catalysis. An overview is given by:

J. Falbe, H. Bahrmann, W. Lipps, D. Mayer, G. D. Frey, Alcohols Aliphatic in Ullmann's Encyclopedia of Industrial Chemistry, 2013 and

D. Sanfilippo, P. N. Rylander, Hydrogenation and Dehydrogenation in Ullmann's Encyclopedia of Industrial Chemistry, 2009.

The hydrogenation process does not have any measurable influence on the isomer distribution, meaning that the skeletal isomers of the aldehyde are found in the same ratio in the alcohol.

The conversion of the alcohol mixture to the ester mixture is preferably effected by esterifying the alcohol mixture with a carboxylic acid or carboxylic anhydride.

These are processes known per se, the details of which can be found in EP1186593B1 and EP1300388B1. The ester mixture can in principle also be prepared by transesterification of an existing ester with the $C_9$ alcohol. EP1430014B1 shows that the process step of esterification has no influence on the quality of the plasticizer; this is determined exclusively by the properties of the $C_9$ alcohol.

The reaction steps of oligomerization, hydroformylation and hydrogenation encompassed by the process are preferably conducted continuously, since the $C_4$ sources used also continuously deliver raw material. Only the esterification step is preferably effected in batchwise operation, since the reaction here is an equilibrium reaction, the equilibrium of which has to be shifted in the direction of the ester via the distillation.

If the alcohol mixture obtained is a mixture of isomeric nonyl alcohols (INA), for example n-nonanol and singly and/or multiply branched nonanols such as methyloctanol in particular, one option is to react this mixture with phthalic acid or phthalic anhydride to give diisononyl phthalate (DINP). The DINP is an ester mixture which can be used as plasticizer for PVC.

The sequence of various process variants is now to be elucidated with reference to simplified flow diagrams. For this purpose, the figures show:

FIG. 7: third variant of the embodiment shown in FIG. 2, in which the hexene is obtained as a by-product of the ethene oligomerization In the first embodiment of the process, shown in FIG. 1B, in a known manner, a feed mixture containing n-butene (C4) is subjected to a first oligomerization (Oli I). This gives rise to an oligomerizate containing various butene oligomers, including dimers, trimers and tetramers of n-butene. The only materials of interest for the process are the dimers of n-butene, the dibutene (2C4), which is a mixture of various $C_8$ olefins. The dibutene (2C4) is separated by distillation from the oligomerizate of the first oligomerization (Oli I), which is not shown in the figure for reasons of simplification.

Figure 1B:
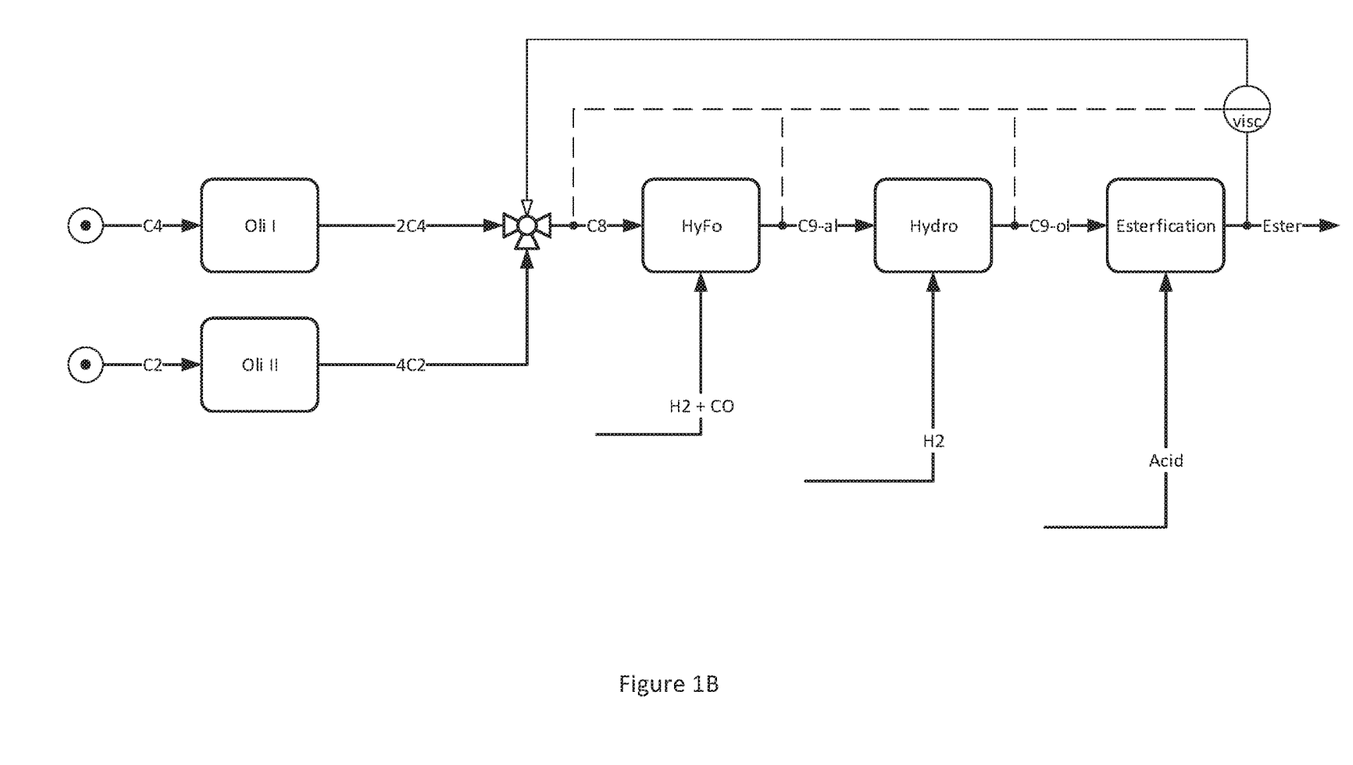
FIG. 1B: first embodiment of the process according to the invention with separate ethene and butene oligomerization

In parallel, a feed mixture containing ethene (C2) is subjected to a second oligomerization (Oli II). The ethene oligomerization (Oli II) and the butene oligomerization (Oli I) proceed in different reactors, i.e. separately from one another in terms of space.

In the second oligomerization (Oli II), various ethene oligomers are formed, including the tetramers of ethene (4C2), which are in turn a mixture of various olefins having eight carbon atoms (C8).

The ethene tetramers (4C2) differ from the dibutene (2C4) by their lower degree of branching.

The ethene and butene oligomers are blended to give a mixture of olefins having eight carbon atoms (C8). This gives rise to a physical mixture of the two types of oligomer. No chemical reaction between the $C_8$ olefins to give higher oligomers takes place because of the lack of catalyst. The addition of the ethene oligomers to the butene oligomers is effected as a function of approximation of the actual viscosity of the process product, the ester mixture (Ester). For this purpose, the approximation of the actual viscosity of the ester mixture is determined by an instrument (visc). The determination is effected by measurement and/or by mathematical prediction from the analysis of the olefin mixture (C8), aldehyde mixture (C9-al) or alcohol mixture (C9-ol) precursors. The mathematical determination is shown as a dotted line in the drawings, and the measurement as a solid line to the instrument (visc).

Since a high proportion of ethene oligomers (4C2) in the mixture of olefins having eight carbon atoms to be hydroformylated (C8) lowers the viscosity of the ester mixture, the proportion of ethene oligomers in the olefin mixture to be hydroformylated (C8) is increased in a controlled manner when the approximation of the actual viscosity determined at the present time exceeds a predetermined target viscosity.

Conversely, the proportion of ethene oligomers in the olefin mixture to be hydroformylated (C8) is reduced in a controlled manner when a comparison of the approximation of the actual viscosity with the target viscosity shows that the actual viscosity is too low.

The adjustment of the mixing ratio of the ethene tetramers (4C2) to the butene dimers (2C4) within the olefin mixture to be hydroformylated C8 is effected manually by the plant operator in the simplest case, and ideally in an automated manner by means of standard closed-loop control technology.

The other process steps for preparation of the ester mixture (Ester) correspond to the prior art outlined with reference to FIG. 1A.

The fact that, downstream after the mixing of the ethene and butene oligomers, the process sequence corresponds to the prior art shows that an existing plant for preparation of ester mixtures based on n-butene can be retrofitted with an acceptable level of cost and complexity for performance of the process according to the invention, namely by installation of the C2 oligomerization (Oli II) and of the apparatus for mixing the ethene and butene oligomers, along with the control thereof as a function of the approximation of the actual viscosity.

Figure 2:
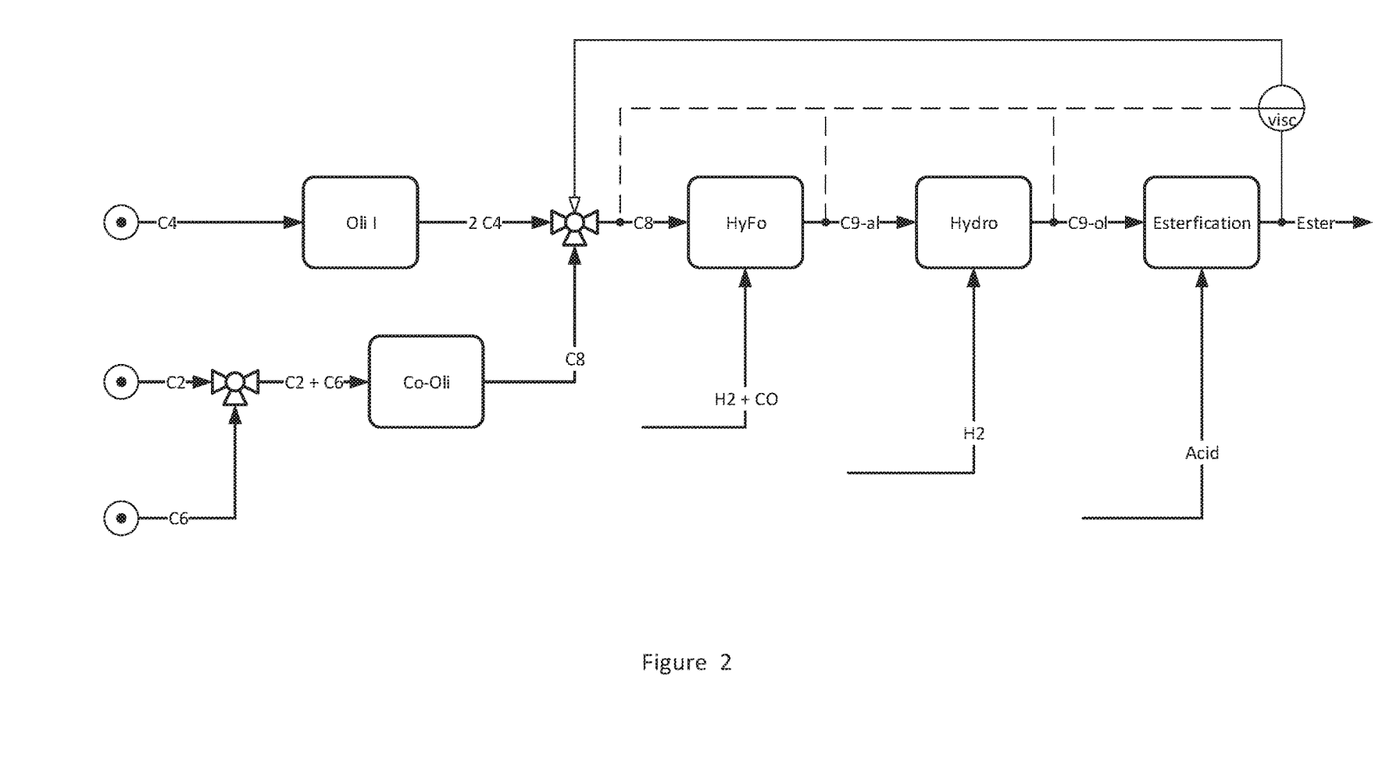
FIG. 2: development of the first embodiment of the process according to the invention, in which the ethene is oligomerized in the presence of hexene

FIG. 2 shows the flow diagram of a preferred development of the embodiment shown in FIG. 1B. This is characterized in that the ethene (C2) is oligomerized in the presence of olefins having six carbon atoms (C6). The second oligomerization is therefore a co-oligomerization (Co-Oli) of ethene and hexene. The co-oligomerization of ethene and hexene has the advantage that the hexene can be used as solvent for the ethene, such that the co-oligomerization can be effected in the liquid phase over a solid catalyst (heterogeneous catalysis). This facilitates the removal of heat from the exothermic reaction via the solvent, increases the process intensity and allows the use of the equipment which is also used for the $C_4$ oligomerization (Oli I). This lowers the development costs. The C8 olefins obtained from the co-oligomerization of ethene and hexene are removed and then—as elucidated with reference to FIG. 1B—added to the dibutene (2C4) in a controlled manner.

Olefins having six carbon atoms (hexene) are not a standard raw material in downstream petrochemistry. However, the hexenes can be prepared by oligomerization of the standard raw materials ethene and propene.

Figure 3:
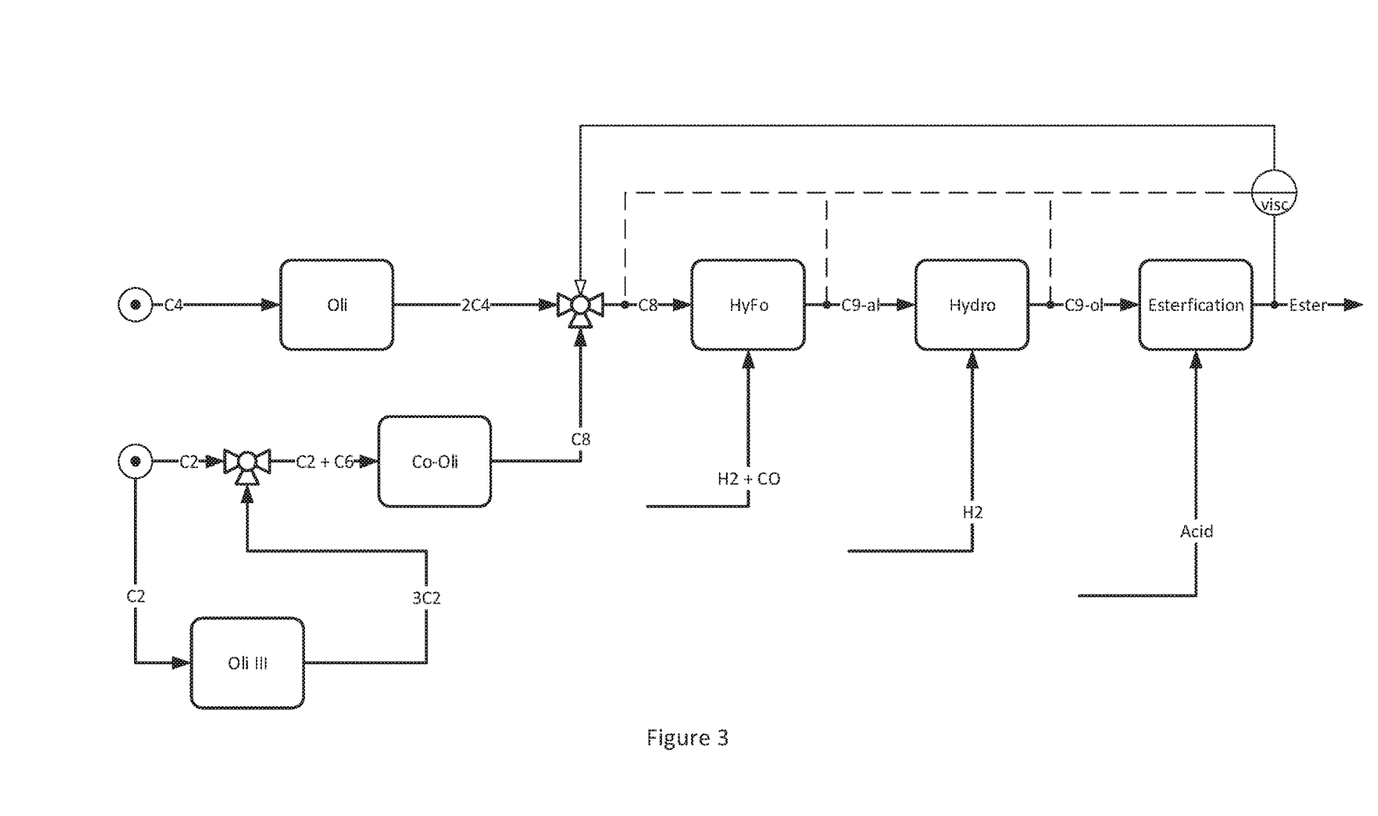
FIG. 3: first variant of the embodiment shown in FIG. 2, in which the hexene is obtained by trimerization of ethene

FIG. 3 shows how the hexene (C6) can be obtained by trimerization of ethene (C2). For this purpose, a portion of the ethene which is required in any case is subjected to a third oligomerization (Oli III) conducted separately from the first and second oligomerizations, and the ethene trimers (3C2) obtained are removed.

Figure 4:
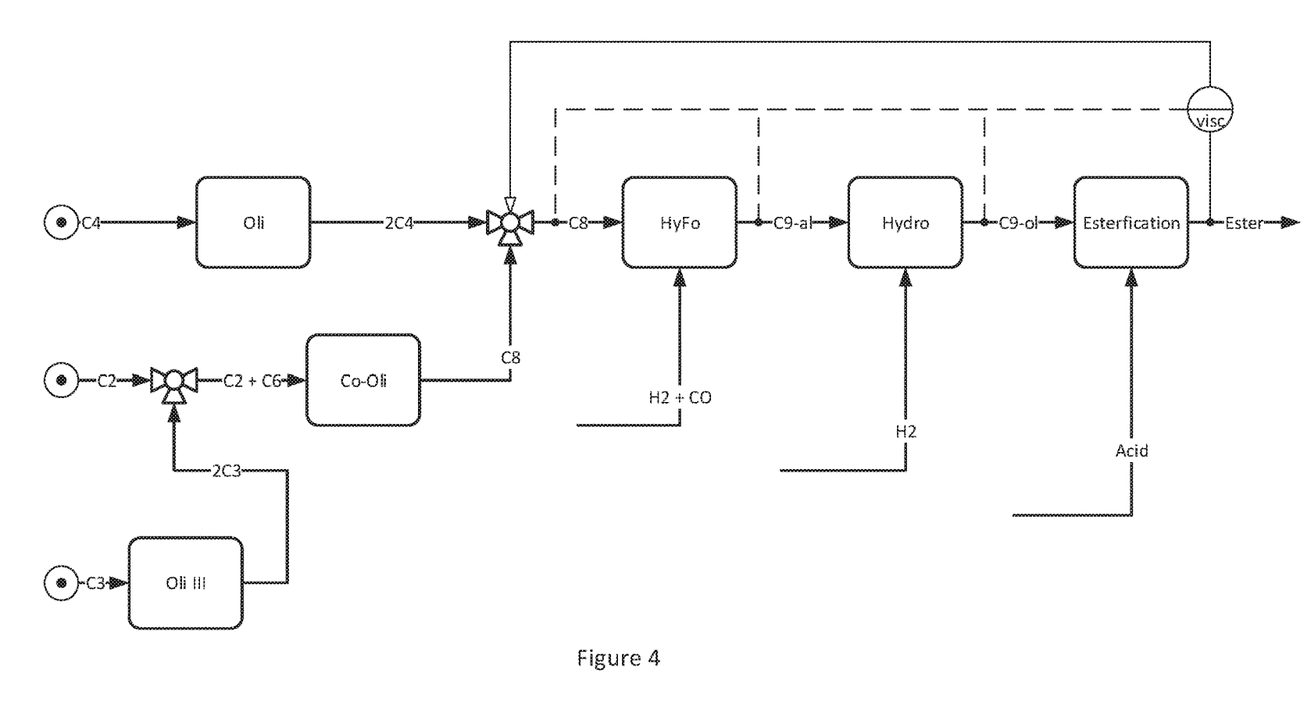
FIG. 4: second variant of the embodiment shown in FIG. 2, in which the hexene is obtained by dimerization of propene

If a $C_3$ source is available as well as the $C_4$ source and the $C_2$ source, the hexene can also be obtained by subjecting propene (C3) to a third oligomerization (Oli III) conducted separately from the first and second oligomerizations. The propene dimers (2C3) formed are removed and co-oligomerized with the ethene. This variant is shown in FIG. 4.

The second embodiment of the invention envisages that the ethene is subjected to a co-oligomerization together with the butene, rather than mixing the oligomers produced separately.

Figure 5:
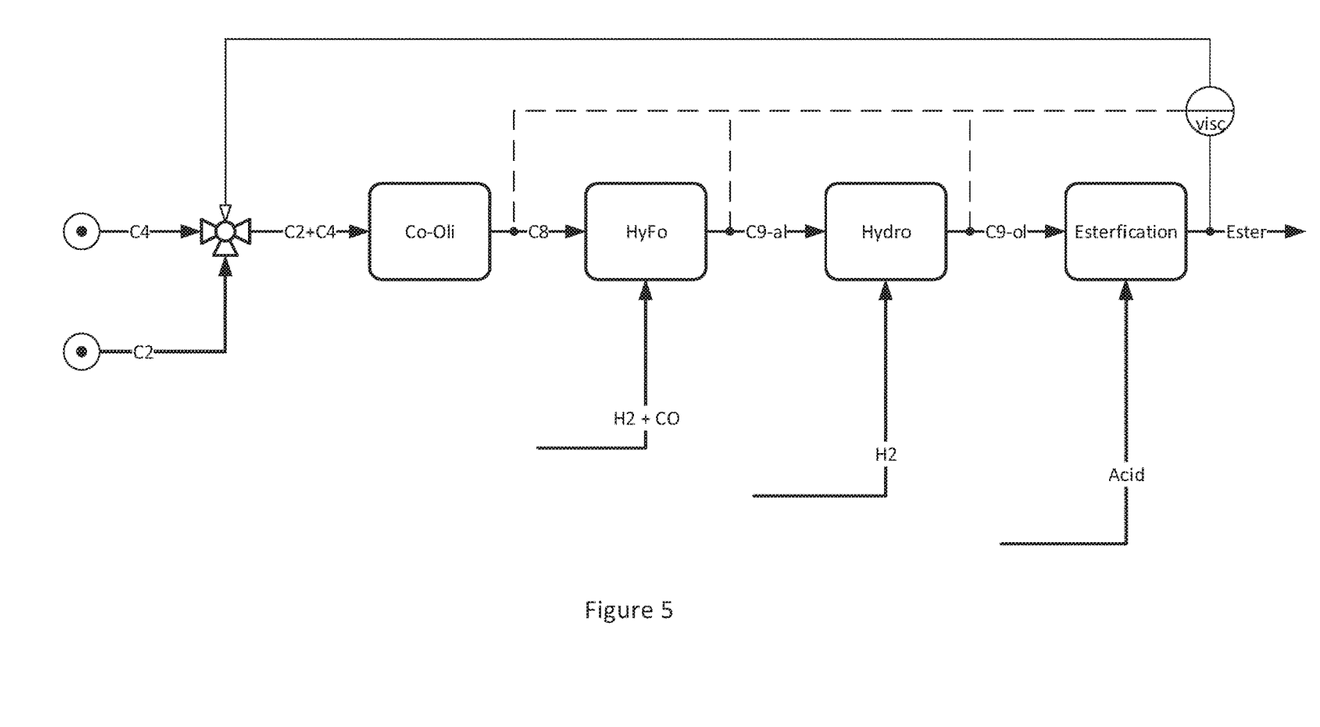
FIG. 5: second embodiment of the process according to the invention with co-oligomerization of ethene and butene

The mixing accordingly takes place before the oligomerization and not thereafter. A corresponding process flow diagram is shown in FIG. 5.

Accordingly, as a function of the approximation of the actual viscosity of the ester mixture, ethene (C2) from a constant C2 source is added to the n-butene-containing feed mixture (C4). If the approximation of the actual viscosity is lower than the predetermined target viscosity, the addition of ethene is throttled. If the comparison shows that the approximation of the actual viscosity is greater than the target viscosity, more ethene is mixed into the n-butene-containing feed mixture.

The mixture comprising n-butene and ethene (C2+C4) is then subjected to a co-oligomerization, conducted in a common reaction vessel.

The olefins having eight carbon atoms (C8) are separated by distillation from the oligomerizate of the co-oligomerization (Co-Oli), which is not shown in the drawing. The C8 olefins then serve as feed material for the hydroformylation (Hydro). The hydroformylation and the other process steps are effected as in the first embodiment.

The fact that, downstream after the mixing of the ethene and the butene, the equipment corresponds to the prior art shows that the existing plant for preparation of ester mixtures based on n-butene can be retrofitted with an acceptable level of cost and complexity for performance of the process, namely by converting the $C_4$ oligomerization to a C2/C4 co-oligomerization, and by installing the apparatus for adding the ethene to the n-butene-containing feed mixture along with the control thereof as a function of the approximation of the actual viscosity.

Figure 6:
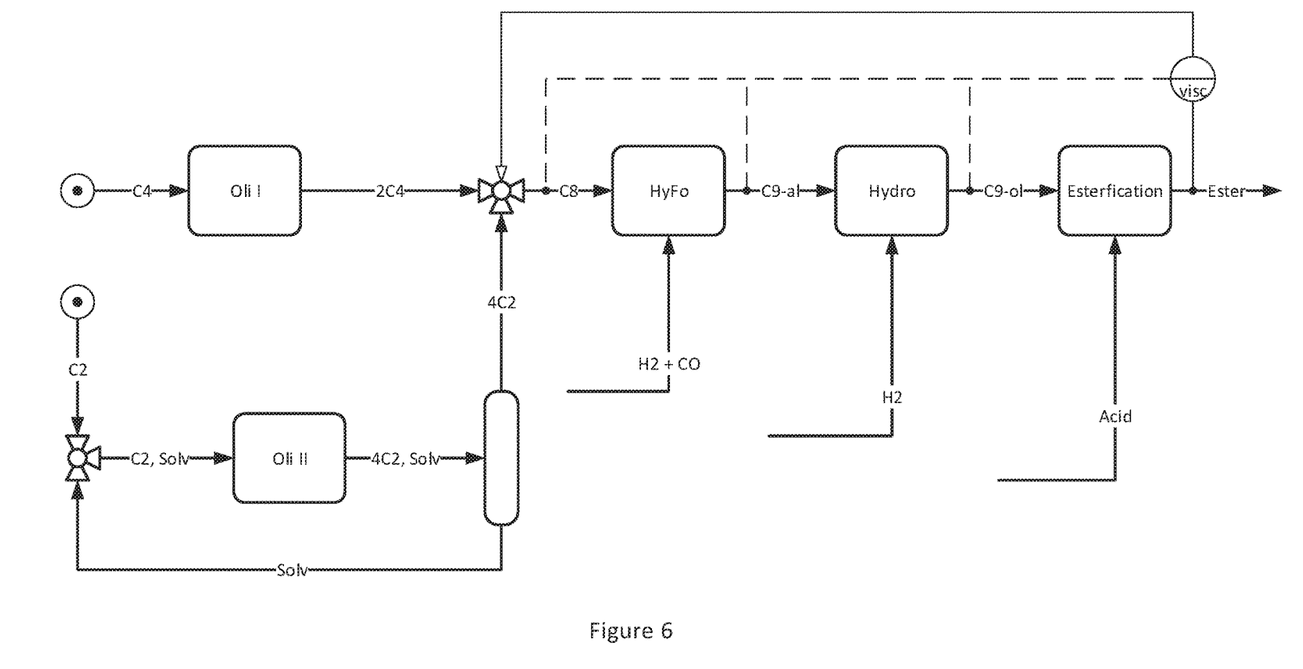
FIG. 6: first embodiment of the process of the invention with separate ethene and butene oligomerization, the ethene oligomerization being effected in the presence of an inert solvent

FIG. 6 shows a specific configuration of the process with separate butene and ethene oligomerization: in order to be able to conduct the second oligomerization (Oli II) in the liquid phase, the ethene (C2) sourced in gaseous form is first dissolved in an inert liquid solvent (Solv). Suitable solvents are particularly alkanes such as propane, isobutane, pentane, hexane, heptane. The ethene oligomerization (Oli II) is then effected within the liquid solvent over the solid heterogeneous catalyst. The ethene tetramers obtained are then present dissolved in the solvent (4C2, Solv). Before the ethene tetramers (4C2) are mixed with the dibutene (2C4), the solvent (sols) has to be removed. This is effected in a distillation column, which is shown here as an exception. The boiling point or boiling range of the solvent should be as far as possible removed from the ethene oligomers, in order to simplify the separation. If it is above the ethene tetramers, these are removed overhead as shown in FIG. 6. The high-boiling solvent remains in the distillation bottoms, and is recycled and mixed with fresh ethene from the $C_2$ source. The rest of the process corresponds to that known from FIG. 1B.

A further embodiment of the process is characterized in that the hexene solvent is obtained as a by-product of the ethene oligomerization.

The reason for this is that new $C_6$ olefin is also formed in turn in the co-oligomerization of ethene and hexene as well as $C_8$. By means of suitable reaction conditions and optionally by virtue of the presence of a further inert solvent, it is possible overall to keep the amount of $C_8$ olefin formed relative to that consumed constant to such an extent that constant circulation is possible. As an alternative, greater amounts of hexene as by-product would also be removed and used in some other way as well as the $C_8$ olefins in each ethene oligomerization.

Figure 7:
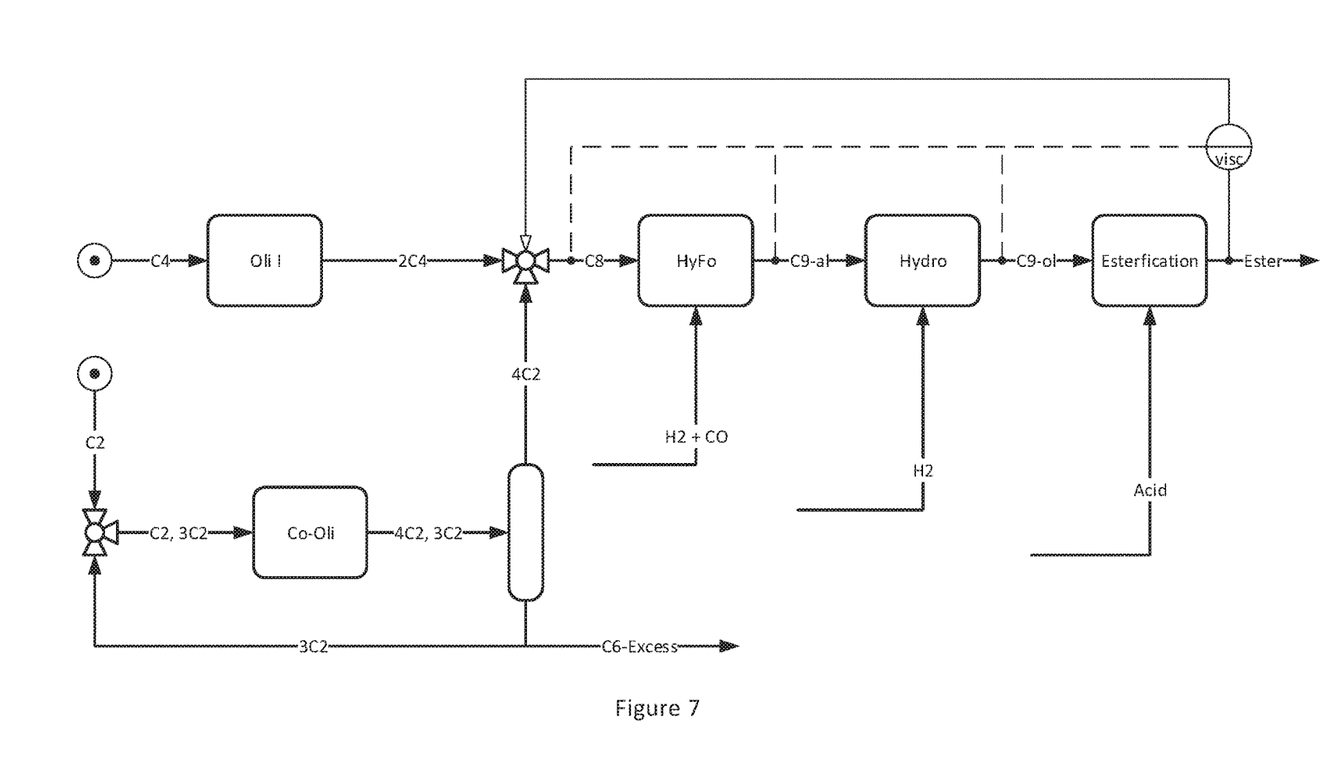

A corresponding process flow diagram is shown in FIG. 7. The apparatus construction corresponds essentially to that shown in FIG. 2. However, the solvent used is not exclusively an inert solvent, but reactive hexene. The hexene comprises trimers of ethene (3C2) which are formed in the co-oligomerization (Co-Oli) of ethene and hexene. The ethene trimers (3C2) which serve as solvent are separated by distillation from the oligomerizate of the co-oligomerization (Co-Oli), at least partly recycled and mixed with fresh ethene. If present, excess hexene (C6-Excess) is discharged and used in some other way. As well as hexene, it is also possible to use an inert solvent in parallel in this process, which is likewise circulated.

The following experimental results show how the viscosity of n-butene-based ester mixtures can be influenced by controlled use of ethene in the preparation of the ester precursors:

EXAMPLE 1

Oligomerization of Butenes to Di-n-Butene 355 g of a heterogeneous catalyst based on nickel and silica-alumina (cf. U.S. Pat. No. 2,581,228) were introduced into an externally oil-heated and -cooled tubular reactor of length 2 m and internal diameter 2.1 cm, which was operated very substantially isothermally. The heat carrier used was the Marlotherm product from Sasol. The reaction was conducted at an absolute pressure of $30*10^5$ Pa in the liquid phase. Subsequently, a feedstock called raffinate III, the composition of which is depicted in Table 1, was run through it in straight pass at a flow rate of 1 kg/h at a tube jacket temperature of 80° C., in the course of which it was oligomerized. After a time of 40 hours, a state in which the conversion no longer changed had been reached.

TABLE 1

| Composition of raffinate III | | | | | |
|---|---|---|---|---|---|
| 1-Butene [% by wt.] | cis-2-Butene [% by wt.] | trans-2-Butene [% by wt.] | n-Butane [% by wt.] | isobutane [% by wt.] | Other substances [% by wt.] |
| 24 to 29 | 11 to 16 | 20 to 24 | 16-18 | 21-23 | less than 0.5 |

Beyond the reaction stage, the oligomers were separated from the butanes and unconverted butenes and analysed for their composition. For identification of the octene skeletal isomers, hydrogenating GC analysis was used, in which the oligomeric olefins were first hydrogenated to alkanes. The alkanes thus obtained were then separated by gas chromatography and detected. It is possible to differentiate between three relevant $C_8$ isomers: linear C8 (formed from n-octenes), singly branched C8 (formed from methylheptenes) and doubly branched C8 (formed from dimethylhexenes). The results are summarized in Table 2.

In order to reflect the overall process in question, the product discharge (about 5 kg) was collected and subjected to distillative separation in order to separate the desired $C_8$ fraction from the remaining lower-boiling unconverted butenes and butanes and the higher-boiling heavier oligomers and by-products. The purified product was provided for the hydroformylation.

EXAMPLE 2

Oligomerization of Ethene in the Solvent Isobutane 263 g of a heterogeneous catalyst based on nickel and silica-alumina (cf. U.S. Pat. No. 2,581,228) were introduced into an externally oil-heated and -cooled tubular reactor of length 2 m and internal diameter 2.1 cm, which had been provided with a thermocouple. Subsequently, a mixture averaging 13% by weight of ethene and 87% by weight of isobutane was run through it in straight pass at a total flow rate of 1 kg/h at a set temperature of 30° C. The pressure was kept constant at $30*10^5$ Pa. After a time of 106 hours, a state in which the conversion no longer changed had been reached. The results of the ethene oligomerization are likewise summarized in Table 2. The product mixture was again collected and the C8 formed was freed of higher- and lower-boiling impurities by distillation and provided for the hydroformylation.

EXAMPLE 3

Co-Oligomerization of Ethene and 1-Hexene in the Solvent n-Hexane 501 g of a heterogeneous catalyst based on nickel and silica-alumina (cf. U.S. Pat. No. 2,581,228) were introduced into an externally oil-heated and -cooled tubular reactor of length 2 m and internal diameter 2.1 cm, which had been provided with a thermocouple. Subsequently, a mixture averaging 10% by weight of ethene, 49% by weight of 1-hexene and 41% by weight of n-hexane was run through it in straight pass at a total flow rate of 1 kg/h at a set temperature of 50° C. The pressure was kept constant at $30*10^5$ Pa. The results of the co-oligomerization of ethene and 1-hexene are likewise summarized in Table 2. The product mixture was again collected and the C8 formed was freed of higher- and lower-boiling impurities by distillation and provided for the hydroformylation.

TABLE 2

| Results of the oligomerization experiments | | | | | | | |
|---|---|---|---|---|---|---|---|
| | | | | | | C8 sel. | |
| Ex. | Feed | WHSV | X(C4) | X(C2) | C8 content | doubly branched | singly branched | linear |
| 1 | C4 | 2.8 h$^{-1}$ | 43% | — | 86% | 25% | 59% | 16% |
| 2 | C2 | 4.7 h$^{-1}$ | — | 99% | 7% | 11% | 48% | 39% |
| 3 | C2 + C6 | 2.0 h$^{-1}$ | — | 87% | 89% | 1% | 25% | 73% |

EXAMPLE 4

Hydroformylation of the Various $C_8$ Olefin Mixtures

In each case 0.013 g of Rh(acac)(CO)$_2$ and 0.67 g of tris(2,4-di-tert-butylphenyl) phosphite were weighed into an argon-inertized 100 ml Schlenk vessel. Subsequently, 50 g of $C_8$ olefin were transferred into the Schlenk vessel in an argon countercurrent. The solution formed was then transferred into a likewise argon-inertized 100 ml autoclave from Parr Instruments. The autoclave was equipped with a sparging stirrer. At the start of the experiment, the stirrer was put into operation at 1200 rpm and synthesis gas (CO/H2=1:1 (% by vol.)) was injected to $20*10^5$ Pa. Subsequently, the autoclave was heated to 120° C. On attainment of the reaction temperature, the synthesis gas pressure was increased to 50*10⁵ Pa. During the reaction, the pressure was kept constant with synthesis gas via closed-loop pressure control. The reaction was conducted for 17 h. Hydroformylation was effected up to full conversion in each case. After the autoclave had been cooled and decompressed, the reaction output was transferred into a 1 l argon-purged Schlenk vessel.

This experiment was conducted a total of five times for each olefin and the five reaction outputs from the individual experiments for one olefin in each case were combined. The three product fractions of the collected reaction outputs were then separated from the catalyst at 100 rpm by means of distillation with the aid of a Heidolph rotary evaporator (Laborota 4002 with ILMVAC pump) at 1 mbar and 120° C., with overhead removal of the products, mixtures of $C_9$ aldehydes. The yields of $C_9$ aldehydes were about 96% in each case.

EXAMPLE 5

Hydrogenation of the Various $C_9$ Aldehydes Mixtures to the Corresponding $C_9$ Alcohol Mixtures 180 g (1.26 mol) of each aldehyde mixture from the hydroformylation were diluted with 150 ml of methanol and cooled to 0° C. Added gradually to this solution while stirring, according to the mass of the aldehyde, were 2 equivalents of sodium borohydride (23.9 g, 0.63 mol, Sigma Aldrich) (corresponding to 1 molar equivalent of $H_2$). On completion of addition, the reaction mixture was stirred at room temperature for 2 h. The product solution was then extracted three times with 200 ml each time of dichloromethane, and the product-containing dichloromethane was washed once again with a saturated ammonium chloride solution. This was followed by drying over sodium sulphate and distillative removal of the dichloromethane from the $C_9$ alcohol mixture. The product yield was about 89% in each case.

EXAMPLE 6

Esterification of the $C_9$ Alcohols with Phthalic Anhydride to Give Diisononyl Phthalate (DINP) and Determination of the Viscosities An apparatus comprising a 250 ml distillation flask with magnetic stirrer bar, sampling stub, water separator with attached jacketed coil condenser and thermometer was initially charged in each case with 37.02 g (0.25 mol) of phthalic anhydride (Sigma Aldrich), 90 mg (0.1 mol % based on phthalic anhydride) of tetrabutyl orthotitanate and 79.34 g (0.55 mol) of a $C_9$ alcohol mixture prepared according to Example 1 to 5, and esterification was effected at 220° C. For rapid removal of water, 40 g of cyclohexane were added as entraining agent. After 7 hours, the reaction had ended. The excess alcohol and the entraining agent were distilled off at 180° C. and a reduced pressure of 3 mbar. This was followed by cooling to 80° C., neutralization with 1 ml of a 10% by weight aqueous NaOH solution in 10 ml of $H_2O$, and stirring at standard pressure for 15 minutes. Thereafter, the mixture was dried at this temperature at 500 Pa and, thereafter, at a temperature of 180° C. and a pressure between 500 Pa and 100 Pa, freed of traces of water and alcohol by introducing nitrogen. After cooling to 80° C., the product was filtered. The purity of the product was determined by means of GC chromatography. The viscosity of the products was measured with a Stabinger™ SVM™ 3000 viscometer (Anton Paar) in accordance with ASTM D 7042.

Measurement of Viscosity According to ASTM D7042

The Stabinger SVM 3000 viscometer is a combination instrument with which density and viscosity can be determined. For this purpose, two measurement cells are connected in series in the instrument. A rotary viscometer with cylinder geometry is installed for determination of the viscosity, and a density measurement cell working by the oscillating U-tube principle for determination of the density. By injecting the sample once, both measurements are thus determined. The samples are analysed at 20° C. The temperature of the measurement cells is controlled via a Peltier element (reproducibility 0.02° C.). The samples are analysed with the preset "MO-ASTM (PRECISE)" analysis mode, measurement with maximum accuracy and repetitions, for tests according to the ASTM D7042 standard. For this purpose, for each measurement, a further about 0.5 ml sample is added (in order to rule out inclusions of air or contamination). In the internal repetitions, a valid result is only displayed once the deviation in the values is not more than +/−0.1% of the measurement for the viscosity and +/−0.0002 g/cm³ for the density. In addition to the internal repetitions, a double determination is conducted for each sample. After each determination, the instrument is cleaned with acetone and dried with air (installed pump).

The results of the viscosity measurements are shown in Table 4.

TABLE 4

Results of the dynamic viscosity measurements

| C8 source$^{(C8\ synthesis\ from\ Ex.\ No.)}$ | Viscosities proceeding from the mixtures of the C8 sources [mPa · s] | | | | |
|---|---|---|---|---|---|
| | 1:0 | 2:1 | 1:1 | 1:2 | 0:1 |
| 2C4 + 4C2$^{(1+2)}$ | 97.5 | 91.6 | 88.8 | 86.2 | 81.5 |
| 2C4 + C8 from C2 + C6$^{(1+3)}$ | 97.5 | 90.3 | 87.1 | 84.1 | 78.7 |

EXAMPLE 7

Co-Oligomerization of Butenes and Ethene

The experiments relating to the oligomerization of the n-butene-containing feedstock raffinate III in direct comparison with the co-oligomerization of ethene with raffinate III were conducted on the laboratory scale in continuously operated fixed bed tubular reactors. For this purpose, 12 g of a heterogeneous catalyst based on nickel and silica-alumina (cf. U.S. Pat. No. 2,581,228) were introduced into an externally oil-heated and -cooled tubular reactor of length 1.6 m and internal diameter 0.7 cm. Subsequently, firstly raffinate III and secondly a mixture of 2% by weight of ethene and 98% by weight of raffinate III were run through it in straight pass at a total flow rate between 75 and 184 g/h at a set temperature of 80° C. The reaction was conducted at an absolute pressure of 28*10⁵ Pa in the liquid phase. The composition of the raffinate III is shown in Table 1. The analysis of the reactor input and output was effected by means of online GC analysis. By variation of the weight hourly space velocity (WHSV) between 1.5 h⁻¹ and 25 h⁻¹, various comparable target conversions were established.

The resulting $C_8$ product selectivity and the selectivities for linear and singly and doubly branched octenes are reproduced in Table 5 by way of example for two different pairs of experiments each with comparable butene conversions. The butene conversions X(C4) were calculated from the difference in the butene content in the reactor input and the butene content in the reactor output (Equation 1). The butenes present in the raffinate input stream and the butenes formed as intermediates through the dimerization of the ethene were considered here with no further differentiation. Ethene was converted to an extent of 100% in the examples adduced here.

$$X_{C4} = (m'_{butenes,0} - m'_{butenes,i}) m'_{butenes,0} \quad \text{(Equation 1)}$$

TABLE 5

Results of the oligomerization of raffinate III in direct comparison with the co-oligomerization raffinate III and ethene.

| | | | | | C8 sel. | | |
|---|---|---|---|---|---|---|---|
| No. | Feed | WHSV | X(C4) | X(C2) | C8 content | doubly branched | singly branched | linear |
| 6a | C4 | 12.5 h$^{-1}$ | 10% | — | 92% | 13% | 57% | 28% |
| 6b | C4 + C2 | 15.3 h$^{-1}$ | 9% | 100% | 50% | 12% | 56% | 31% |
| 6c | C4 | 6.3 h$^{-1}$ | 14% | — | 91% | 15% | 58% | 24% |
| 6d | C4 + C2 | 9.2 h$^{-1}$ | 13% | 100% | 56% | 14% | 57% | 27% |

CONCLUSION

In the comparison of the $C_8$ isomers in Table 2, it quickly becomes clear that the oligomerization of pure ethene and the co-oligomerization of ethene with hexene leads to more linear and far fewer doubly branched $C_8$ olefins. If the results of the viscosity measurements of the esterified products synthesized therefrom are consulted, it becomes clear that the higher proportion of linear and the lower proportion of doubly branched $C_8$ olefins as a result of the use of ethene leads to lowering of the viscosities of the corresponding plasticizers as a function of the amounts of ethene used. A virtually linear relationship can be recognized between the falling viscosity and the increasing proportion of ethene-based $C_8$ mixtures.

The direct comparison of pure butene oligomerization with the co-oligomerization of 2% ethene with 98% butene shows that the selectivity for linear $C_8$ olefin with about equal conversions in each case is about 2% higher in the co-oligomerization, and the selectivity for the doubly branched $C_8$ olefin is 1% lower than in the pure butene oligomerization. According to the relationships shown in the previous examples between the linearity of the $C_8$ olefins and the viscosity of the later plasticizer that results therefrom, a lower viscosity of the plasticizer is thus also to be expected in the co-oligomerization of ethene with butenes as a result of the positive effect of the ethene.

LIST OF REFERENCE SYMBOLS

C4 olefins having four carbon atoms
Oli oligomerization
C8 olefins having eight carbon atoms
2C4 dibutene
HyFo hydroformylation
H2 hydrogen
CO carbon monoxide
H2+CO synthesis gas
C9-al aldehydes having nine carbon atoms
Hydro hydrogenation
C9-ol alcohols having nine carbon atoms
Esterification
Acid or anhydride
Ester mixture
Visc instrument for determining viscosity
Oli I first oligomerization
C2 ethene
Oli II second oligomerization
4C2 tetramers of ethene
Co-Oli co-oligomerization
C6 olefins having six carbon atoms
3C2 trimers of ethene
C3 propene
2C3 dimers of propene
C4+C2 mixture comprising n-butene and ethene
Solv solvent
C2, Solv ethene, dissolved in the solvent
4C2, Solv tetramers of ethene, dissolved in the solvent
C2+C6 mixture comprising ethene and n-hexene
4C2, 3C2 tetramers of ethene, dissolved in trimers of ethene
C6-Excess olefins having six carbon atoms formed in excess

What is claimed is:

1. Process for preparing an ester mixture in which an n-butene-containing feed mixture having a composition which varies over time is subjected to a first oligomerization to obtain an oligomerizate and at least some of the butene oligomers present in the oligomerizate are hydroformylated to aldehydes, of which at least some are hydrogenated by subsequent hydrogenation to an alcohol mixture which is then converted to the ester mixture, and in which an approximation of the actual viscosity of the ester mixture is determined, characterized in that ethene oligomers which are obtained by subjecting an n-butene-free, ethene-containing and hexene-containing feed mixture to a second oligomerization conducted separately from the first oligomerization are added in a controlled manner to the butene oligomers to be hydroformylated, such that the second oligomerization is a co-oligomerization of ethene and hexene.

2. Process according to claim 1, characterized in that
    a) the hexene is sourced from a third oligomerization which is conducted separately from the first and second oligomerizations, in which propene is dimerized, or
    b) the hexene is sourced from a third oligomerization which is conducted separately from the first and second oligomerizations, in which ethene is trimerized; or
    c) the hexene is sourced from the second oligomerization.

3. Process according to claim 1, characterized in that the second oligomerization is effected in the presence of a liquid inert solvent in which the ethene is at least partly dissolved and which is separated from the ethene oligomers after the second oligomerization has been conducted.

4. Process according to claim 1, characterized in that the controlled addition of the ethene oligomers to the butene oligomers to be hydroformylated is effected in such a way that a target viscosity of the ester mixture is first fixed, the approximation of the actual viscosity of the ester mixture determined is compared with the target viscosity of the ester mixture, and the amount of the ethene oligomers added to the butene oligomers to be hydroformylated is increased if the approximation of the actual viscosity is greater than the target viscosity, or the amount of the ethene oligomers added to the butene oligomers to be hydroformylated is reduced if the approximation of the actual viscosity is less than the target viscosity.

5. Process according to claim 1, characterized in that the approximation of the actual viscosity of the ester mixture is determined by measuring the viscosity of the ester mixture.

6. Process according to claim 1, characterized in that the approximation of the actual viscosity of the ester mixture is determined by calculation, the calculation being based on analysis of the alcohol mixture, on an analysis of the aldehydes to be hydrogenated, or on an analysis of the oligomers to be hydroformylated.

7. Process according claim 1, characterized in that the n-butene-containing feed mixture is composed of a combination of the following substance mass flow rates which vary within the specified substance mass flow rate ranges with a respective rate of variation within the specified range of rates of variation:

| Substance | Substance mass flow rate | Rate of variation |
|---|---|---|
| Isobutene: | 0 kg/s to 1 kg/s | $-0.05$ g/s$^2$ to $0.05$ g/s$^2$ |
| 1-Butene: | 0 kg/s to 6 kg/s | $-0.30$ g/s$^2$ to $0.30$ g/s$^2$ |
| 2-Butene (cis + trans): | 1 kg/s to 13 kg/s | $-0.30$ g/s$^2$ to $0.30$ g/s$^2$ |
| Isobutane: | 0 kg/s to 3 kg/s | $-0.15$ g/s$^2$ to $0.15$ g/s$^2$ |
| n-Butane: | 1 kg/s to 7 kg/s | $-0.30$ g/s$^2$ to $0.30$ g/s$^2$ |
| Other materials: | 0 kg/s to 1 kg/s | $-0.05$ g/s$^2$ to $0.05$ g/s$^2$. |

8. Process according to claim 1, characterized in that the first oligomerization and/or the second and/or the third oligomerization is effected in the presence of a heterogeneous catalyst containing nickel, silicon and aluminium.

9. Process according to claim 1, characterized in that the hydroformylation is conducted in the presence of a homogeneous catalyst system comprising
either cobalt or rhodium.

10. Process according to claim 1, characterized in that the conversion of the alcohol mixture to the ester mixture is effected by esterifying the alcohol mixture with a carboxylic acid or carboxylic anhydride, or by obtaining the ester mixture by means of a transesterification of an existing ester with the alcohol mixture.

11. Process according to claim 10, characterized in that the alcohol mixture is a mixture of isomeric nonyl alcohols which is reacted with phthalic acid or phthalic anhydride to give diisononyl phthalate.

* * * * *